(12) United States Patent
Fähsing

(10) Patent No.: US 12,004,798 B2
(45) Date of Patent: Jun. 11, 2024

(54) GENERATOR FOR THE DELIVERY OF HIGH FREQUENCY ALTERNATING CURRENT TO A MEDICAL INSTRUMENT

(71) Applicant: OLYMPUS WINTER & IBE GMBH, Hamburg (DE)

(72) Inventor: Thomas Fähsing, Blankenburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 636 days.

(21) Appl. No.: 16/493,646

(22) PCT Filed: May 4, 2018

(86) PCT No.: PCT/EP2018/061551
§ 371 (c)(1),
(2) Date: Sep. 12, 2019

(87) PCT Pub. No.: WO2018/202872
PCT Pub. Date: Nov. 8, 2018

(65) Prior Publication Data
US 2020/0000506 A1 Jan. 2, 2020

(30) Foreign Application Priority Data

May 4, 2017 (DE) ............... 10 2017 109 638.8

(51) Int. Cl.
*A61B 18/12* (2006.01)
*A61B 18/00* (2006.01)
(52) U.S. Cl.
CPC ............ *A61B 18/1206* (2013.01); *A61B 2018/00589* (2013.01); *A61B 2018/00601* (2013.01);
(Continued)

(58) Field of Classification Search
CPC ...... A61B 18/1206; A61B 2018/00589; A61B 2018/00601; A61B 2018/00607;
(Continued)

(56) References Cited

U.S. PATENT DOCUMENTS 3,058,470 A 10/1962 Seeliger et al.
4,748,419 A * 5/1988 Somerville ............... H03K 5/26
330/10

(Continued)

FOREIGN PATENT DOCUMENTS

CH 348483 A 8/1960
CN 102727303 A 10/2012
(Continued)

OTHER PUBLICATIONS

Jun. 27, 2018 Written Opinion issued in International Application No. PCT/EP2018/061551.
(Continued)

*Primary Examiner* — Daniel W Fowler
*Assistant Examiner* — Lindsay Regan Lancaster
(74) *Attorney, Agent, or Firm* — Oliff PLC

(57) ABSTRACT

A generator for the delivery of high frequency alternating current to a medical instrument has a power supply unit, a high frequency generator primary unit (HF generator primary unit), an application unit, and a control unit. The HF generator primary unit is connected to the power supply unit and the application unit and designed to supply the application unit with high frequency alternating current during operation. The application unit is electrically connected in a switchable manner to connections for connecting a medical instrument via at least one relay. The control unit is galvanically separated from the application unit and designed to control the at least one relay and the application unit as applicable. The control unit is connected to the application
(Continued)

Figure 1:
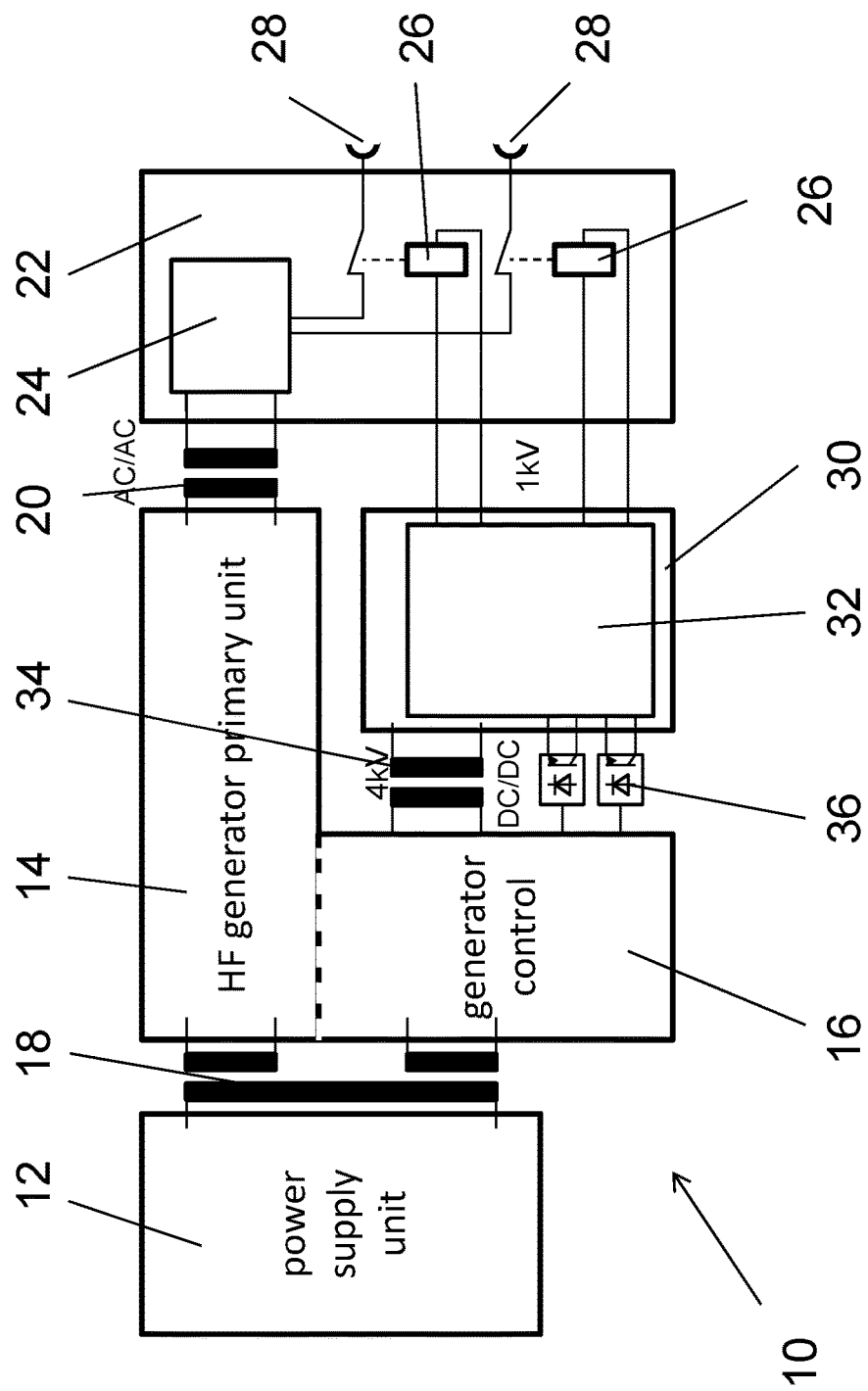

unit via an intermediate control circuit, wherein the intermediate control circuit is galvanically separated both from the control unit and from the application unit.

21 Claims, 2 Drawing Sheets

(52) U.S. Cl.
CPC ............. *A61B 2018/00607* (2013.01); *A61B 2018/1226* (2013.01); *A61B 18/1233* (2013.01); *A61B 2018/1266* (2013.01); *A61B 2018/1286* (2013.01); *A61B 2018/1293* (2013.01)

(58) Field of Classification Search
CPC .... A61B 2018/1226; A61B 2018/1266; A61B 2018/1286; A61B 2018/1293
See application file for complete search history.

(56) References Cited

U.S. PATENT DOCUMENTS

| | | | | |
|---|---|---|---|---|
| 5,627,758 | A * | 5/1997 | Lansberry | ............... B60L 50/60 318/400.17 |
| 6,261,285 | B1 * | 7/2001 | Novak | ............... A61B 18/1206 606/34 |
| 2003/0036757 | A1 * | 2/2003 | Novak | ............... A61B 18/1233 606/41 |
| 2004/0030328 | A1 * | 2/2004 | Eggers | ............... A61B 18/1206 606/49 |
| 2004/0257086 | A1 * | 12/2004 | Montrose | .............. B81C 99/005 324/420 |
| 2005/0101947 | A1 | 5/2005 | Jarrard et al. | |
| 2013/0110103 | A1 * | 5/2013 | Assmus | .................. A61B 18/12 606/37 |
| 2014/0191624 | A1 * | 7/2014 | Jahshan | .................... H02P 6/14 310/68 B |
| 2015/0162837 | A1 * | 6/2015 | Duan | ................ H02M 3/33569 363/21.14 |
| 2015/0164576 | A1 | 6/2015 | Gilbert | |
| 2016/0213416 | A1 | 7/2016 | Stein | |
| 2016/0296271 | A1 | 10/2016 | Danziger et al. | |

FOREIGN PATENT DOCUMENTS

| | | |
|---|---|---|
| CN | 105592813 A | 5/2016 |
| DE | 3329582 A1 | 3/1985 |
| DE | 3427517 A1 | 1/1986 |
| DE | 102010025298 A1 | 12/2011 |
| JP | H08-275957 A | 10/1996 |
| JP | 2001-276089 A | 10/2001 |
| JP | 2003-526385 A | 9/2003 |

OTHER PUBLICATIONS

Jan. 8, 2018 Office Action issued in German Application No. DE 102017109638.8.
Jun. 27, 2018 International Search Report issued in International Application No. PCT/EP2018/061551.
Mar. 16, 2022 Office Action issued in Japanese Patent Application No. 2019-553896.
Jan. 6, 2022 Office Action issued in Chinese Patent Application No. 201880019787.2.
Apr. 4, 2023 Office Action issued in European Patent Application No. 18 722 520.6-1113.

\* cited by examiner

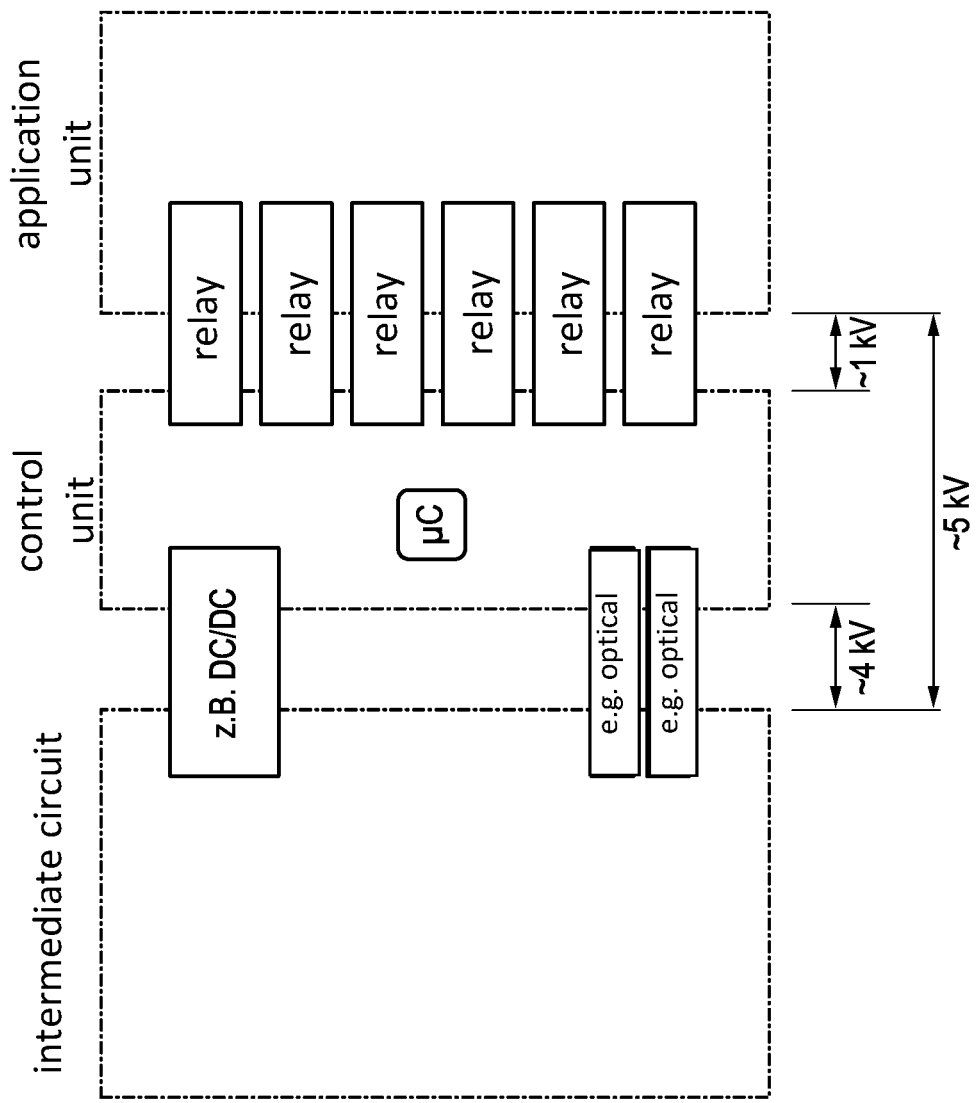

GENERATOR FOR THE DELIVERY OF HIGH FREQUENCY ALTERNATING CURRENT TO A MEDICAL INSTRUMENT

The invention relates to a generator for the delivery of high frequency alternating current to a medical instrument, for example for cutting and/or coagulating biological tissue. The generator comprises terminals to which a corresponding instrument can be connected, in order to electrically connect the instrument to the generator and to supply high frequency alternating current to the instrument during operation. Together, the generator and the instrument form a high frequency or HF surgical device.

High frequency or HF surgical devices have long been known from prior art. The HF energy that is generated by the HF surgical device and output during operation is for example used for cutting or coagulating on the human body. In order to be used, an electrosurgical instrument, by means of which the HF energy is applied to the tissue, is connected to the generator. In case of a monopolar application, a separate neutral or return electrode, which returns the energy to the HF surgical device, is connected as well. In case of a bipolar application, the return electrode is arranged at the instrument.

Modern generators for HF surgical devices, which meet the current safety requirements, have an application unit and an intermediate circuit that is galvanically separated from the application unit. The electrosurgical instrument is connected to an application unit of the generator. Thus, during the electrosurgical application, the application unit is in direct contact with the tissue of a patient. For the safety of the patient and the user, the application unit and the intermediate circuit are galvanically separated from each other. An example of such an HF surgical device is described in DE 10 2010 025298 A1.

It is the object of the present invention to provide an improved HF surgical device that offers a high level of operational safety.

Pursuant to the invention, this object is achieved by means of a generator for the delivery of high frequency alternating current to a medical instrument, wherein the generator has a power supply unit, a high frequency generator primary unit (HF generator primary unit), an application unit, and a control unit. According to the invention, the HF generator primary unit is connected to the power supply unit and the application unit and designed to supply the application unit with high frequency alternating current during operation. The application unit is electrically connected in a switchable manner to terminals for connecting a medical instrument via at least one relay. The control unit is galvanically separated from the application unit and designed to control the at least one relay and the application unit as applicable. The control unit is connected to the application unit via an intermediate control circuit, wherein the intermediate control circuit is galvanically separated both from the control unit and from the application unit.

An intermediate control circuit pursuant to the invention has the advantage that the relay coils and the read-back contacts of the relays controlled by the intermediate control circuit can be realized with substantially smaller isolation distances. As a result, for example relays with smaller dimensions can be used. This saves both space and weight. The reason why smaller isolation distances are possible is that the intermediate control circuit may be designed such that the maximum potential difference between the application unit and the intermediate control circuit—and, therefore, the isolation voltage for which the relays must be designed—can be smaller if the intermediate control circuit is galvanically separated from the control unit of the generator so that a greater maximum potential difference may already exist between the intermediate circuit of the generator and the intermediate control circuit. At said interface, such a greater maximum potential difference requires less effort for obtaining a correspondingly high isolation voltage.

The HF primary unit and the control unit may be realized on a circuit board and form a primary supply and control unit. In that case, the intermediate control circuit forms a secondary control unit that is galvanically separated from the primary supply and control unit and controls and reads the outputs of the relays that switch the application unit.

Preferably, the voltage of the intermediate control circuit is supplied by transformers arranged between the intermediate control circuit and the control unit, for example DC transformers such as DC/DC converters.

Transformers such as optocouplers are preferably provided for the transmission of signals from the control unit to the intermediary control circuit.

Preferably, the intermediary control circuit has a relay control unit, for example a controller, that, on one side, is connected to the at least one relay in order to control it and to read its read-back contacts. On the other side, the relay control unit is connected to the control unit via the transformer—for example the optocoupler—and is thus able to exchange signals with the control unit.

Since the relay control unit may be designed as a controller, the number of signal transformers, for example the number of optocouplers, that are provided between the intermediate control circuit and the control unit may be smaller than the number of relays to be controlled, since, via the signal transformers, more complex, encoded signals are able to be transmitted, which can be decoded by the relay control unit and be transformed into relay control signals for several relays. This also contributes to the fact that only a few high voltage resistant components, such as optocouplers or DC/DC converters, need to be provided between the control unit and the intermediate control circuit. This makes it easier to realize an isolation voltage of more than 2 kV, for example more than 4 kV, between the control unit and the intermediate control circuit. On the other hand, this allows the isolation voltage between the intermediate control circuit and the application unit to be limited to a maximum of 1 kV, so that the relay as well only needs to be designed for this isolation voltage.

The application unit of the generator preferably has a high frequency generator circuit that, together with the HF generator primary unit, forms a high voltage transformer, so that the application unit is galvanically separated from the HF generator primary unit as well. This once again makes it possible to operate the HF generator primary unit and the control unit at the same potential level, so that the control unit and the HF generator primary unit do not need to be galvanically separated.

In the following, the invention shall be explained in more detail based on an exemplary embodiment with reference to the figures. The figures show the following:

FIG. 1 a schematic block diagram of a generator pursuant to the invention, and

FIG. 2 a second schematic illustration of the generator pursuant to the invention.

The generator 10 shown in FIG. 1 has a power supply unit 12 that is connected to an HF generator primary unit 14 and a control unit 16 of the generator 10 and supplies these components of the generator with energy. The HF generator primary unit 14 and the control unit 16 may, for example, be connected to the power supply unit 12 via a transformer 18. However, the power supply unit 12 may also be a battery power supply unit or another type of power supply unit.

A primary coil of a high frequency transformer 20, the secondary side of which is part of an application unit 22, is part of the HF generator primary unit 16. The application unit 22 has a high frequency generator circuit 24 designed to generate high frequency voltage that may, for example, be supplied to a medical instrument connected to the generator 10 during operation. To this end, the high frequency generator circuit 24 is connected via relays 26 to terminals 28 for connecting one or more medical instruments. The terminal between the high frequency generator circuit 24 and the terminals 28 can be switched via the relay 26.

The control of the relay 26 and the reading of its read-out contacts is performed via an intermediate control circuit 30 having a relay control unit 32. First of all, the intermediate control circuit 30 is connected to the control unit 16, namely via a DC/DC converter 34 on the one hand and via optocouplers 36 on the other. As a result, the intermediate control circuit 30 is galvanically separated from the control unit 16. The DC/DC converter 34 serves the purpose of supplying energy to the intermediate control circuit 30. The optocouplers 36 serve the purpose of transmitting control signals between the control unit 14 and the relay control unit 32 of the intermediate control circuit 30.

The relay control unit 32 is designed to transform control signals received by the control unit 16 via the optocouplers 36 into relay control signals through which the relays 26 can be controlled individually. In addition, the relay control unit 32 is able to read the read-back contacts of the relays 26 and to generate the corresponding control signals, which the relay control unit 32 can transmit to the control unit 16 via the optocouplers 36. The optocouplers 36 and the DC/DC converter 34 as well as the corresponding distances between the intermediate control circuit 30 and the control unit 16 are chosen such that the isolation voltage between the control unit 16 and the intermediate control circuit 30 is for example 4 kV. On the other hand, the isolation voltage between the intermediate control circuit 30 and the application circuit 22 only has to be for example 1 kV so that it is sufficient to dimension the relays 26 for an isolation voltage of 1 kV and not for the maximum output voltage of the generator 10 of, for example, 5 kV.

LIST OF REFERENCE NUMBERS

10 Generator
12 Power supply unit
14 High frequency generator primary unit (HF generator primary unit)
16 Control unit
18 Transformer
20 High frequency transformer
22 Application unit
24 High frequency generator circuit
26 Relay
28 Terminals
30 Intermediate control circuit
32 Relay control unit
34 DC/DC converter
36 Optocoupler

The invention claimed is:

1. A generator configured to deliver high frequency (HF) alternating current to a medical instrument, the generator comprising:
   a power supply unit;
   an HF generator primary unit;
   an application unit;
   at least one relay that is configured to switchably, electrically connect the application unit to at least one terminal of the medical instrument;
   a control unit configured to control the application unit and the at least one relay; and
   an intermediate control unit configured to receive control signals from the control unit, process the control signals and transmit the control signals, after processing, to the application unit, wherein:
   the power supply unit is configured to supply power to the HF generator primary unit and the control unit;
   the HF generator primary unit is connected to, but galvanically separated from, the power supply unit and the application unit and is configured to supply the application unit with HF alternating current during operation of the generator;
   the control unit is configured to control the at least one relay and the application unit via the intermediate control unit;
   the control unit is galvanically separated from the intermediate control unit by a first galvanic separation and the intermediate control unit is galvanically separated from the application unit by a second galvanic separation such that the first galvanic separation and the second galvanic separation are two serial galvanic separations in a control circuit from the control unit to the application unit, the first galvanic separation being before an entry of the intermediate control unit and the second galvanic separation being at an outlet of the intermediate control unit; and
   the control unit, the intermediate control unit and the application unit are configured such that the control signals from the control unit for controlling the application unit are transmitted over the first galvanic separation from the control unit to the intermediate control unit and from the intermediate control unit over the second galvanic separation to the application unit.

2. The pursuant to claim 1, wherein the intermediate control circuit is configured to receive, during the operation of the generator, the control signals from the control unit and to generate relay control signals in dependence on the control signals and to output the relay control signals to the at least one relay.

3. The pursuant to claim 2, wherein:
   the intermediate control circuit is connected to the control unit via at least one optocoupler,
   the at least one optocoupler is configured to transmit the control signals from the control unit to the intermediate control circuit, and
   the intermediate control circuit has a relay control unit that is configured to process the control signals received from the control unit and to generate the relay control signals in dependence on the control signals.

4. The pursuant to claim 3, wherein a number of optocouplers of the at least one optocoupler between the control unit and the intermediate control circuit is smaller than a number of relays of the at least one relay.

5. The generator pursuant to claim 1, wherein an isolation voltage between the control unit and the intermediate control circuit is higher than 2 kilovolt, and an isolation voltage between the intermediate control circuit and the application unit is no higher than 1 kV.

6. The generator pursuant to claim 1, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

7. The generator pursuant to claim 2, wherein an isolation voltage between the control unit and the intermediate control circuit is higher than 2 kilovolt, and an isolation voltage between the intermediate control circuit and the application unit is no higher than 1 kV.

8. The generator pursuant to claim 3, wherein an isolation voltage between the control unit and the intermediate control circuit is higher than 2 kilovolt, and an isolation voltage between the intermediate control circuit and the application unit is no higher than 1 kV.

9. The generator pursuant to claim 4, wherein an isolation voltage between the control unit and the intermediate control circuit is higher than 2 kilovolt, and an isolation voltage between the intermediate control circuit and the application unit is no higher than 1 kV.

10. The generator pursuant to claim 2, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

11. The generator pursuant to claim 3, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

12. The generator pursuant to claim 4, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

13. The generator pursuant to claim 5, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

14. The generator pursuant to claim 7, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

15. The generator pursuant to claim 8, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

16. The generator pursuant to claim 9, wherein
the application unit has a high frequency generator circuit that is connected to the HF generator primary unit and configured to supply a connected medical instrument with high frequency high voltage during operation, and
the high frequency generator circuit is electrically connected in a switchable manner to the at least one terminal for connecting the connected medical instrument via the at least one relay.

17. The generator pursuant to claim 1, wherein the intermediate control unit controls a read-back contact of the at least one relay.

18. The generator pursuant to claim 1, wherein a circuit board includes the control unit and the HF generator primary unit and is galvanically separated from the power supply unit and the intermediate control circuit.

19. The generator pursuant to claim 1, wherein:
the intermediate control circuit includes a relay control unit; and
the relay control unit is configured to transform control signals from the control unit to relay control signals for the relay.

20. A generator configured to delivery high frequency (HF) alternating current to a medical instrument, the generator comprising:
a power supply unit;
an HF generator primary unit;
an application unit;
at least one relay that is configured to switchably, electrically connect the application unit to at least one terminal of the medical instrument;
a control unit configured to control the application unit and the at least one relay; and
an intermediate control unit configured to receive control signals from the control unit, process the control signals and transmit the control signals, after processing, to the application unit, wherein:
the power supply unit is configured to supply power to the HF generator primary unit and the control unit;
the HF generator primary unit is connected to, but galvanically separated from, the power supply unit and the application unit and is configured to supply the application unit with HF alternating current during operation of the generator;
the control unit is configured to control the at least one relay and the application unit via the intermediate control unit;
the control unit is galvanically separated from the intermediate control unit by a first galvanic separation and the intermediate control unit is galvanically separated from the application unit by a second galvanic separation such that the first galvanic separation and the second galvanic separation are two serial galvanic separations in a control circuit from the control unit to the application unit, the first galvanic separation being before an entry of the intermediate control unit and the second galvanic separation being at an outlet of the intermediate control unit;

the intermediate control unit is configured to control a read-back contact of the at least one relay;

the intermediate control circuit is configured to receive, during the operation of the generator, the control signals from the control unit and to generate relay control signals in dependence on the control signals and to output the relay control signals to the at least one relay;

the intermediate control circuit is connected to the control unit via at least one optocoupler;

the at least one optocoupler is configured to transmit the control signals from the control unit to the intermediate control circuit;

the intermediate control circuit has a relay control unit that is configured to process the control signals received from the control unit and to generate the relay control signals in dependence on the control signals; and a number of optocouplers of the at least one optocoupler between the control unit and the intermediate control circuit is smaller than a number of relays of the at least one relay.

21. A generator configured to deliver high frequency (HF) alternating current to a medical instrument, the generator comprising:

a power supply unit;
an HF generator primary unit;
an application unit;
at least one relay that is configured to switchably, electrically connect the application unit to at least one terminal of the medical instrument;
a control unit configured to control the application unit and the at least one relay; and
an intermediate control unit configured to receive control signals from the control unit, process the control signals and transmit the control signals, after processing, to the application unit, wherein:

the power supply unit is configured to supply power to the HF generator primary unit and the control unit;

the HF generator primary unit is connected to, but galvanically separated from, the power supply unit and the application unit and is configured to supply the application unit with HF alternating current during operation of the generator;

the control unit is configured to control the at least one relay and the application unit via the intermediate control unit;

the control unit is galvanically separated from the intermediate control unit by a first galvanic separation and the intermediate control unit is galvanically separated from the application unit by a second galvanic separation such that the first galvanic separation and the second galvanic separation are two serial galvanic separations in a control circuit from the control unit to the application unit, the first galvanic separation being before an entry of the intermediate control unit and the second galvanic separation being at an outlet of the intermediate control unit;

the control unit, the intermediate control unit and the application unit are configured such that the control signals from the control unit for controlling the application unit are transmitted over the first galvanic separation from the control unit to the intermediate control unit and from the intermediate control unit over the second galvanic separation to the application unit;

the application unit has a high frequency generator circuit that is connected to the HF generator primary unit and configured to supply a connected medical instrument with high frequency high voltage during operation;

the high frequency generator circuit is electrically connected in a switchable manner to the at least one terminal for connecting the connected medical instrument via the at least one relay;

the intermediate control unit is configured to control the at least one relay and read the output of the at least one relay; and the at least one relay is a separate component from the intermediate control unit.

* * * * *